Figure 2A:
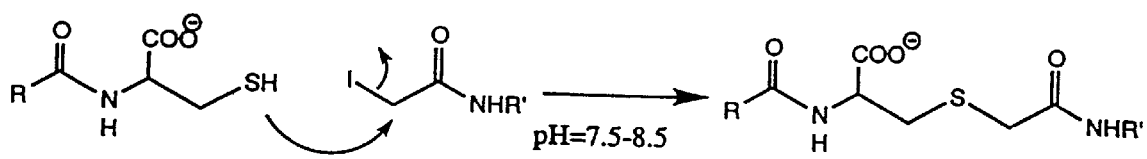
Figure 2B:
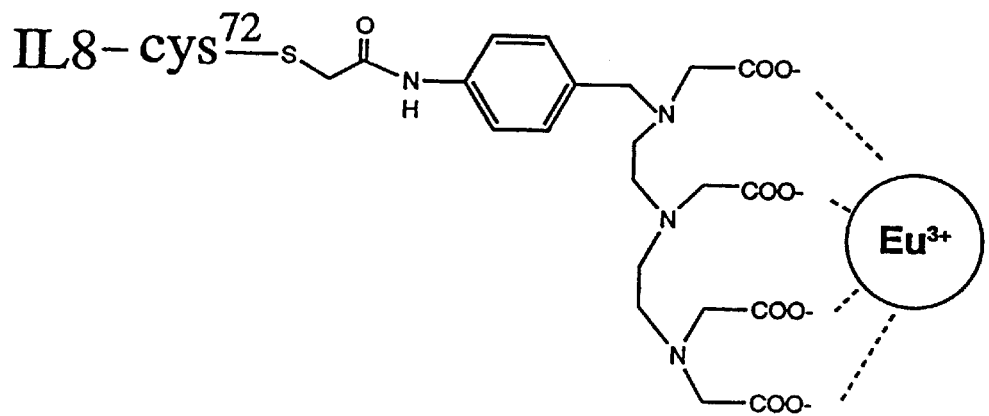

United States Patent [19]
Inglese et al.

[11] Patent Number: 6,156,520
[45] Date of Patent: *Dec. 5, 2000

[54] SITE-SPECIFIC BIOCONJUGATES OF CHEMOKINES AND THEIR USE IN ASSAYS

[75] Inventors: James Inglese, Dayton; Kenneth C. Appell, Skillman; Philippe Samama, Lawrenceville; Ilana L. Stroke; Jonathan J. Burbaum, both of Cranbury, all of N.J.

[73] Assignee: Pharmacopeia, Inc., Cranbury, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/911,762

[22] Filed: Aug. 15, 1997

Related U.S. Application Data

[63] Continuation-in-part of application No. 08/868,280, Jun. 3, 1997.

[51] Int. Cl.[7] ...................................................... G01N 33/53
[52] U.S. Cl. .......................... 435/7.1; 435/7.2; 435/7.24; 435/7.8; 435/7.9; 435/7.92; 435/7.93; 435/7.95; 530/324; 530/402
[58] Field of Search ............................ 435/7.1, 7.2, 7.24, 435/7.8, 7.9, 7.92, 7.93, 7.95; 530/324, 402

[56] References Cited

PUBLICATIONS

Martin et al. "On the Nature of Cysteine Coordination to CuA in Cytochrome c Oxidase", *Journal of Biological Chemistry*, vol. 263, No. 17(Jun. 15, 1988), pp. 8420–9. QP501.J7.

Marquez et al."Covalent Modification of a Critical Sulfhydryl Group in the Acetylcholine Receptor: Cysteine–222 of the Alpha–Subunit" *Biochemistry*, vol. 28, No. 18(Sep. 5, 1989), pp. 7433–9. QP501.B52.

Soini, E. and Lövgren, T. (1987) *CRC Crit. Rev. Anal. Chem. 18*, 105–154.

Baldwin et al. (1991) *Proc. Natl. Acad. Sci USA 88*, 502–506, Abstract.

Bacon, K.B. and Schall, T.J. (1996) *Int. Arch. Allergy Immunol. 109*, 97–109.

Baggiolini, M. and Clark–Lewis, I., (1992) *FEBS Lett. 307*, 97–101.

Holmes, W.E. et al. (1991) *Science 253*, 1278–1280.

Murphy, P. M. and Tiffany, H. L. (1991) *Science 253*, 1280–1283.

Strieter et al., (1994) *J. Lab. Clin. Med. 123*, 183–197.

Sekido N. et al., (1993) *Nature 365*, 654–657.

Leonard, E.J. et al. (1991) *J. Invest. Dermatol. 96*, 690–694.

Braunwalder et al., (1996) *Anal. Biochem. 238*, 159–164.

Takeuchi, T., et al., (1995) *Anal. Chem. 67*, 2655–8.

Alouani, S., et al. (1995) *Eur. J. Biochem. 227*, 328–334.

Matsushima, K., et al. (1988) *J. Exp. Med 167*, 1883–1893, abstract.

Clark–Lewis et al. (1994) *J. Biol. Chem. 23*, 16075–16081.

Horuk, R. et al. (1994) *Immunology Today 15*, 169–174.

Baggiolini et al. (1997) *Annu. Rev. Immunol. 15*, 675–705.

Hébert et al. (1991) by *The American Society for Biochemistry and Molecular Biology*, Inc. 266, 18989–18994.

Mottram et al. (1990) *American Clinical Laboratory*, 4 pages.

Mukkala et al. (1989) *Analytical Biochemistry 176*, 319–325.

Daly et al. (1995) *The Journal of Biological Chemistry*, vol. 270, No. 40, 23282–23292.

Lusti–Narasimhan et al. (1996) *The Journal of Biological Chemistry*, vol. 271, No. 6, 3148–3153.

Webb et al., "Time–Resolved Fluorescence: A Multilabel Alternative to the Use of Single Label Radionucleotides Assays for Screening", Wallace—Plate Counter Product Line, 23 pages.

*Primary Examiner*—Jeffrey Stucker
*Attorney, Agent, or Firm*—Heslin & Rothenberg, P.C.

[57] ABSTRACT

The present invention encompasses polypeptides that comprise a chemokine receptor binding sequence and are useful in determining the affinity of a compound for a chemokine receptor. Substitution of one of the amino acids of the C-terminal region of the polypeptide with a cysteine enables the polypeptide to be detectably labelled without loss of receptor binding activity and without the problems inherent in radioiodine labelling. Methods for use of the polypeptides in competitive binding assays are also disclosed.

21 Claims, 4 Drawing Sheets

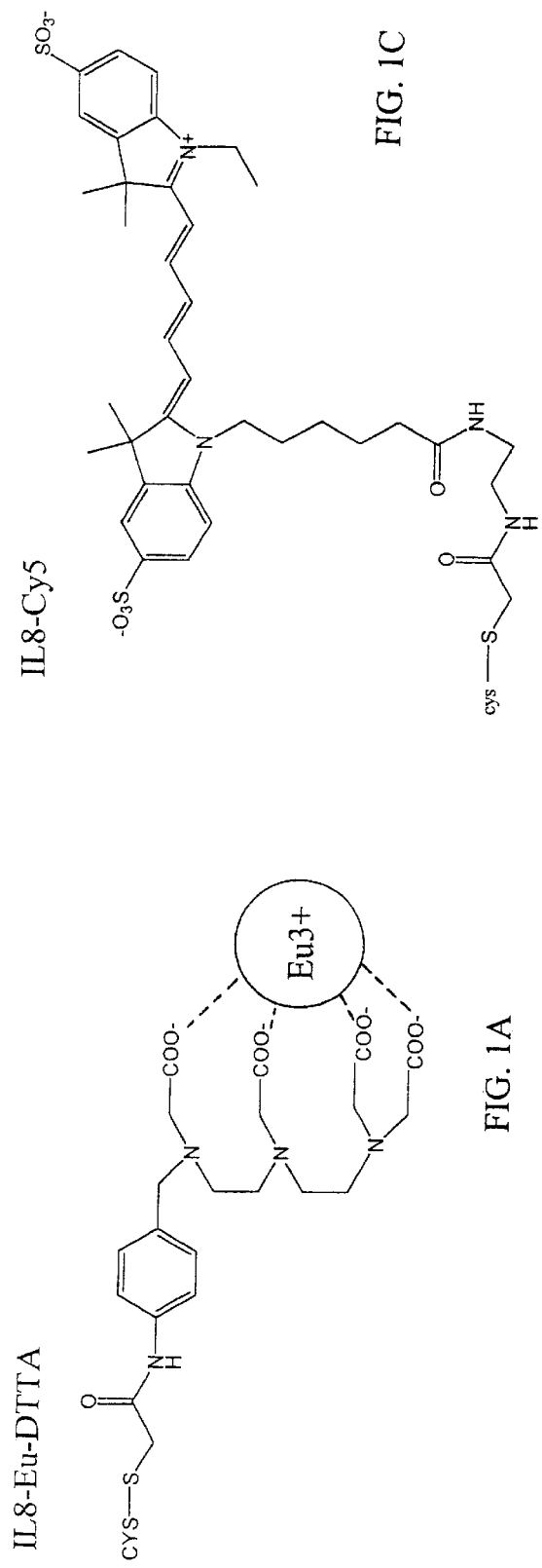
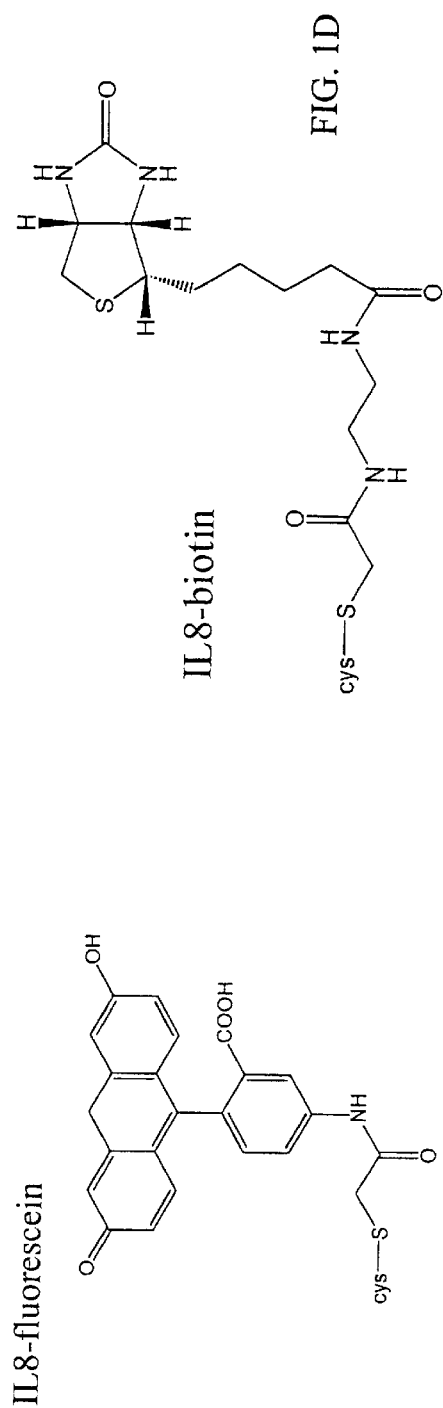
FIG. 1A  IL8-Eu-DTTA
FIG. 1B  IL8-fluorescein
FIG. 1C  IL8-Cy5
FIG. 1D  IL8-biotin

FIG. 4

|  |  | IL8cys72-Eu$^{3+}$ | [$^{125}$I]-IL8 |
|---|---|---|---|
| CXC R1 | $K_D$ | 1.4 ± 0.5 (3) | 1.9 (1) |
|  | $B_{max}$ | 180 ± 100 (3) | 260 (1) |
|  | $K_I$(IL8) | 5 (1) | nd |
|  | $K_I$(GROα) | 370 (1) | nd |
| CXC R2 | $K_D$ | 2.4 ± 1.1 (4) | 2.8 (1) |
|  | $B_{max}$ | 500 ± 100 (4) | 600 (1) |
|  | $K_I$(IL8) | 3.7 ± 2.4 (4) | 2.3 ± 0.8 (4) |
|  | $K_I$(GROα) | 3.3 ± 0.8 (3) | 1.9 (1) |
|  | $K_I$(IL8cys72) | nd | 2.2 ± 1.1 (2) |
|  | $K_I$(IL8cys72-biotin) | nd | 2 (1) |

SITE-SPECIFIC BIOCONJUGATES OF CHEMOKINES AND THEIR USE IN ASSAYS

CROSS-REFERENCE TO RELATED APPLICATIONS

This application is a continuation-in-part of application Ser. No. 08/868,280, filed on Jun. 3, 1997.

FIELD OF THE INVENTION

The present invention relates to the screening of compounds for binding to receptors for which chemokines are ligands, and reagents useful in such screening.

BACKGROUND OF THE INVENTION

Chemokines are small cytokines having similar structures. There are two types of chemokines: those of the CXC type and those of the CC type, in which four conserved cysteines are linked by disulfide bonds. In the CXC type, the first two cysteines are separated by one amino acid, whereas in the CC type they are not. The two types of chemokines are well known, and described, for example, by Baggioloini et al., 1997.

Interleukin-8 (IL-8) is a representative, well-studied chemokine that is produced by a variety of cell types involved in inflammatory settings. It is known to act on neutrophilic polymorphonuclear leukocytes (neutrophils), promoting their migration to the site of inflammation and causing their subsequent activation (Bacon, K. B. and Schall, T. J. (1996) *Int. Arch. Allergy Immunol.* 109, 97–109; Baggiolini, M. and Clark-Lewis, I., (1992) *FEBS Lett.* 307, 97–101). Two receptor subtypes (A and B, also called CXC R1 and CXC R2) are currently known to mediate IL-8 action in cells (Holmes, W. E. et al. (1991) *Science* 253, 1278–1280; Murphy, P. M. and Tiffany, H. L. (1991) *Science* 253, 1280–1283). In contrast with receptors for other interleukins, these molecules belong to the large family of seven-transmembrane G protein-coupled receptors.

The amount of IL-8 (and other chemokines) is elevated in a variety of morbid conditions, including lung diseases such as cystic fibrosis and adult respiratory distress syndrome, atherosclerosis, psoriasis, rheumatoid arthritis and reperfusion injury (Strieter et al., (1994) *J. Lab. Clin. Med.* 123, 183–197). The causal role of IL-8 in the onset of inflammation has been demonstrated in animal models (Sekido N. et al., (1993) *Nature* 365, 654–657; Leonard, E. J. et al. (1991) *J. Invest. Dermatol.* 96, 690–694).

This body of evidence has led to efforts to discover antagonists of IL-8 binding to its specific cell surface receptors. Such antagonists are candidates as therapeutic agents for IL-8-dependent disorders. For example, IL-8 labelled with $^{125}$I has been used in assays for binding to CHO membranes to determine IL-8 antagonists, as described in WO 9625157. However, $^{125}$I is a dangerous reagent, posing significant handling and disposal problems. In addition, radioactively iodinated reagents decay when stored for long periods, and cannot be used thereafter. Also, enzymatic processes for radioactively iodinating peptides can, under certain circumstances, cause a loss in binding activity.

Lanthanides are fluorescent labels that have been used primarily in clinical diagnostic kits in standard immunoassay formats; i.e., they have been used to label antibodies for use in such kits. For example, they are conventionally used in time-resolved fluorescent assays for clinical screening. Multiple lanthanide labels (Europium, Samarium, Terbium, and Dysprosmium) can be used in the same assay, and distinguished by their differing emission wavelength/decay time fluorescent profiles. Thus, different analytes can be determined in the same assay using these different labels.

The fluorescent properties of lanthanide probes make them particularly useful in biological assays (Soini, E. and Loevgren, T. (1987) *CRC Crit. Rev. Anal. Chem.* 18, 105–153). Specifically, the extended fluorescence lifetime of lanthanides allows measurement of signal to be made after the decay of shorter-lived background fluorescence originating from either the biological sample or the plastic support. For example, Eu-labelled anti-phosphotyrosine has been used in a sensitive protein tyrosine kinase assay (Braunwalder et al., (1996) *Anal. Biochem.* 238, 159–164). Also, Takeuchi, T., et al., ((1995) *Anal. Chem.* 67, 2655–8) have described a lanthanide-labelled benzodiazepine used in receptor binding assays.

To find lead compounds for drug discovery programs, large numbers of compounds are often screened for their activity as enzyme inhibitors or receptor agonists/antagonists. Large libraries of compounds are needed for such screening. As a result of developments in this field, it is now possible to simultaneously produce combinatorial libraries containing hundreds of thousands of small molecules for screening. With the availability of such libraries, however, has come a need for large-scale, rapid screening methods.

Lanthanide reagents would appear to be potentially useful in high throughput screening of such libraries to measure the binding of chemokines to their receptors. Conjugation of lanthanide chelates, and other detectable labels, to chemokines, however, can, and has, resulted in substantial loss of binding affinity.

In an attempt to obtain a fluorescently labelled IL-8, Alouani, S., et al. (1995) *Eur. J. Biochem.* 227, 328–334 specifically labelled the amino terminus of IL-8 by first oxidizing the serine at amino acid position no. 1 under mild periodate oxidation conditions and reacting the resultant glyoxylyl with an amino-oxy derivative of fluorescein. The resultant fluorescein-labelled IL-8 had a 10-fold lower affinity than $[^{125}I]$IL-8 for IL-8 receptors. Thus, binding of IL-8 was substantially lost with fluorescein isothiocyanate labeling.

Similarly, modification of a cysteine at position 25 of IL-8 by addition of a fluorescent nitrobenzoxadiazol iodoacetamide (NBD) was found to lower affinity of the fluorescently labelled IL-8 by two orders of magnitude. (Lusti-Narasimhan et al. (1996) *J. Biol. Chem.* 271, 3148–3153).

IL-8 can be prepared containing lanthanide fluorescent labels conjugated to IL-8 at available lysine groups. This method, however, can modify lysine residues that are critical to the receptor-ligand interaction. Thus, while the resulting reagent may be useful for a competitive immunoassay for determining the amount of IL-8 in a sample, it is less acceptable for use in a competitive assay to measure receptor/ligand binding.

It is therefore an object of the invention to label a polypeptide having the binding affinity of a CC or CXC chemokine without substantially decreasing that affinity.

It is also an object of the invention to obtain a labelled reagent that avoids the handling and disposal problems associated with $^{125}$I.

It is also an object of the invention to provide an assay that is easily adaptable for high throughput screening of potential CC and CXC chemokine receptor ligands.

It is another object of the invention to provide a labelled reagent that can be stored for considerable periods of time without loss of activity.

SUMMARY OF THE INVENTION

It has been determined that by placing a cysteine residue in the carboxy terminal α-helical region of a polypeptide containing the receptor binding sequence of a chemokine, preferably a CC or CXC chemokine, detectable labels can advantageously be conjugated to the peptide without substantial loss of affinity for receptor.

BRIEF DESCRIPTION OF THE DRAWINGS

FIG. 1A depicts the conjugation of cysteine to an Eu chelate of N1-(p-benzoic acid)-diethylenetriamine-N1, N2, N3 tetraacetic acid (DTTA).

FIG. 1B shows cysteine conjugated to fluorescein.

FIG. 1C depicts cysteine conjugated to the fluorescent label Cy5.

FIG. 1D shows cysteine conjugated to biotin, which can then be bound to an avidin or streptavidin coupled detectable label.

FIG. 2 depicts the sulfhydryl chemistry of lanthanide-labelled IL-8. In FIG. 2A nucleophilic attack of thiol or thiolate upon the alpha carbon of a monosubstituted haloacetamide under neutral pH generates the resultant thioether linkage. FIG. 2B shows the structure of IL-8ser72cys-DTTA-$Eu^{3+}$, and shows the tetraacetic acid-$Eu^{3+}$ chelate conjugated to the carboxyl terminus of the IL-8cys72 mutant.

FIG. 3 shows a chromatographic analysis of IL-8, IL-8cys72 and oxidized IL-8cys72. Graph (a) is a HPLC chromatogram of a coinjection of wild type IL-8 (peak 1) and IL-8cys72 (peak 2) obtained after perfusion cation-exchange chromatography purification. Graph (b) is a HPLC analysis showing IL-8cys72, and graph (c) shows the formation of an oxidized form of IL-8cys72. Graph (d) shows the reduction of the oxidized species back to the reduced form with 100 mM βME.

FIG. 4 is a table of constants obtained in experiments of binding to IL-8 receptors CXC R1 and CXC R2 by Europium labelled IL-8 according to the invention and by $^{125}I$ labelled IL-8.

DETAILED DESCRIPTION OF THE INVENTION

All patents, patent applications, and publications listed herein are hereby incorporated by reference.

The present invention relates to a detectably labelled polypeptide that retains the binding activity of a CC or CXC chemokine. The invention avoids the safety problems associated with radioactive iodine labelling of such chemokines, and avoids the loss of binding activity that occurs with non-radioactive labeling techniques that have been employed.

The polypeptide contains a labelled cysteine in its C-terminal alpha-helix sequence., preferably in its 19 carboxy terminal amino acids, more preferably in its 6 carboxy terminal amino acids. Most preferably, the cysteine is substituted for the C-terminal serine, such as that at amino acid position 72 of IL-8. It is understood that the C-terminal sequence may change somewhat from its helical structure once the cysteine is included.

CC chemokines that can be advantageously labelled according to the present invention include SDF-1, IL-8, GROα, GROβ, GROγ, NAP-2, ENA78, GCP-2, PF4, IP10, Mig, CKα1, and CKα2, and corresponding polypeptides having the receptor binding sequences of those chemokines. CXC chemokines that can be advantageously labelled according to the present invention include MCP-1, MCP-3, Eotaxin, MCP-2, MCP-4, CFβ6, I-309, MIP-1α, MIP-1β, CKβ7, HCC-1, HCC-3, HCC-2, CDβ8, RANTES, CKβ12, TARC, CKβ13, CKβ4, CKβ11, and CKβ9. Labelling of IL-8 is discussed below as an example of the labelling of CC and CXC chemokines.

Preferably the label is fluorescent, but non-fluorescent labels, such as enzymatic and chemiluminescent labels, can also be used without affecting binding activity. For example, it is possible to employ biotin conjugates of cysteine that allow conventional detection following reaction with an avidin or streptavidin coupled label. FIG. 1D shows the embodiment of the invention in which cysteine is conjugated to biotin. For example, enzymatic labels such as horseradish peroxidase or alkaline phosphatase can be conjugated to streptavidin, and used for detection. It is also possible to employ isotopically labelled streptavidin. Use of $^{125}I$ labelled streptavidin avoids the iodination reaction required in conventional iodination of chemokines.

Fluorescent labels are preferred for use in the invention, and any suitable fluorescent label can be used. Examples include cyanine dyes such as Cy-5, Cy-5.5, and Cy7 (Amersham Corp.), fluorescein, rhodamine and Texas red. FIGS. 1B and 1C show embodiments of the invention wherein cysteine is conjugated to fluorescein or Cy5.

Where a cell based assay is to be performed using a fluorescent label, it is preferred that the label fluoresce at a relatively high wavelength, i.e., higher than about 450 nm, to avoid fluorescence interference originating from cells, glass and plastic containers. The labels most preferably fluoresce above 600 nm, and at less than about 800 nm. Labels that excite at about 400 nm can avoid photobleaching caused by near-UV light.

The preferred fluorescent labels are lanthanides. Such labels, and reagents for labelling IL-8 and other chemokines, are commercially available, for example from EG&G Wallac. The labelling reagent used for conjugating the cysteine of the IL-8 polypeptide can be any reagent suitable for sulfhydryl conjugation. One example is the iodoacetamide derivative of the Eu-chelate of N1-(p-benzoic acid)-diethylenetriamine-N1, N2, N3-tetraacetic acid (DTTA) used to form the conjugate of FIG. 1A.

The chemistry of formation of such a Europium-labelled IL-8 is shown in FIG. 2. FIG. 2A depicts the nucleophilic attack of thiol or thiolate upon the alpha carbon of a monosubstituted haloacetamide under neutral pH to generate a thioester linkage. FIG. 2B shows the label linked to IL-8 cysteine, where cysteine is substituted at amino acid 72.

The polypeptide having chemokine activity need only comprise the sequences of the chemokine that are essential for receptor binding. Features of IL-8 are described below as examples of the embodiments of the invention related to chemokines.

The amino acid sequence of IL-8 is well known, and described, e.g., in Matsunshima, K., et al. (1988) *J. Exp. Med.* 167, 1883–1893, and Schmid, J. & Weissmann, C. (1987) *J. Immunol.* 139, 250–256. The structural features of IL-8 are also known, having been determined by Nuclear Magnetic Resonance, X-ray crystallography (Baldwin et al. (1991) *Proc. Natl. Acad. Sci. USA* 88, 502–506) and site-directed mutagenesis studies. Literature concerning IL-8 describes tertiary structures characterized by a disordered amino terminus followed by three antiparallel β-strands connected to a carboxyl terminal α-helix by a β-turn. The β-strands are rigidly held in place by the two intramolecular disulfide bonds. Several regions of the IL-8 molecule have been found to be essential for receptor binding and activation (Clark-Lewis et al. (1994) *J. Biol. Chem.* 23, 16075–16081). Residues in the N-terminal loop ($Ile_{10}$-$Phe_{17}$ & $Leu_{49}$) as well as residues found in the central β-sheet ($Leu_{25}$) define receptor specificity (Horuk, R. et al. (1994) *Immunology Today* 15, 169–174). Deletion of the last six amino acids of the carboxyl terminal α-helix of IL-8 has been found to result in about a ten-fold decrease in affinity for CXCR2 expressed in CHO cells (Daly et al., (1995) *J. Biol. Chem.* 40, 23282–23292), although single alanine substitution of amino acids in this region have been found to have no effect on binding (Hebert et al., 1991) *J. Biol. Chem.* 266, 18989–18994).

In one embodiment, the polypeptide of the invention comprises the β-pleated sheet region of IL-8 from amino acid 10 to amino acid 51, in order to incorporate the residues in the N-terminal loop $Ile_{10}$-$Phe_{17}$ & $Leu_{49}$. In another embodiment, the polypeptide comprises the sequence of IL-8 with fewer than 10, preferably fewer than 3, conservative amino acid substitutions. Conservative amino acid substitutions are well known in the art. In another embodiment, the IL-8 molecule comprises the full length sequence of a IL-8, having between one and three amino acids substituted, deleted, or added in its carboxy terminal 19 amino acids, more preferably in its carboxy terminal 6 amino acids.

The invention also encompasses use of the labelled polypeptides of the invention in methods for determining ligands that bind to the chemokine receptor. Such assays are well known in the art using, e.g., iodinated IL-8. An example of such an assay is shown below. For example, in a method of the invention, a compound to be screened for affinity for IL-8 receptor is contacted with IL-8 receptor in the presence of the labelled polypeptide of the invention. Binding of the polypeptide to the receptor is measured by determining the presence of the label.

The assay can be conducted in a homogeneous manner (i.e., without a liquid separation step) or in a heterogeneous manner (i.e., including a separation step). A preferred homogeneous assay is described in parent application Ser. No. 08/828,280, filed on Jun. 3, 1997, the contents of which have been incorporated by reference herein. Another homogeneous assay is described in Ser. No. 08/553,056, published as WO 97/16569.

Most preferably, the method of the invention is carried out as part of a high throughput screening of a library of compounds for binding to chemokine receptor. The method is particularly advantageous in such screening in that disposal of large amounts of radioactive reagent is avoided. Thus, in one embodiment of the invention, the method is carried out with a plurality of compounds to be screened, preferably at least about 96 compounds, such as when using a 96 well microtitre plate. Such assays can also be performed in the 1536 well plate described in U.S. patent application Ser. No. 60/037,636, filed Feb. 18, 1997. The library of compounds to be screened can be quite large, e.g., containing more than 100,000 compounds.

It is preferred that the compounds assayed in the high throughput method be derived from combinatorial libraries on polymer beads. By synthesizing sufficient compound on each bead for a few assays, compound handling is reduced or eliminated.

Preferably, the library compounds are eluted from the beads and evaporated to dryness in microtiter plates in preparation for the assay. Compounds on beads can be released by photocleavage, or another type of cleavage. Cleavage of photocleavable linkers is preferred. Such linkers, and methods for their cleavage, are described in Barany et al. (1985) *J. Am. Chem. Soc.* 107:4936. Examples of other linkers and the relevant cleavage reagents are described in WO 94/08051.

Using combinatorial libraries prepared on beads, the identity of active compounds is preferably determined using the encoding system described in WO 94/08051, and in U.S. patent applications Ser. Nos. 08/436,120 and 08/239,302 (which correspond to WO 95/30642). In this system, chemical tags encoding the identities of the compounds are applied to the solid supports. The identity of the compound on a given support can be determined by detaching the chemical tags from the support, identifying the tags by, e.g., gas chromatography, and correlating the identities of tags with the identity of the compound. Once an active compound is identified, the corresponding bead (which had contained the compound) can be examined, and the identity of the compound determined by releasing the tags and decoding by this method.

The invention is illustrated by the following Examples, which are intended to merely exemplify the invention and not to limit its scope.

EXAMPLE 1

Formation of Lanthanide Labelled IL-8 and Use in Assay

Materials and Methods

Materials

Eu-chelate of N1-(p-iodoacetamidobenzyl)-diethylenetriamine-N1, N2, N3-tetraacetic acid (DTTA), enhancement solution for measuring $Eu^{3+}$, and Optiphase scintillation fluid were obtained from EG & G Wallac, Inc. (Gaithersburg, Md.). pET30b was obtained from Novagen, Inc. (Madison, Wis.). Microtiter plates were from Costar. [$^{125}$I]IL-8 was obtained from Dupont/NEN, Research Products (Boston, Mass.). CHO K1 cells were obtained from the American Type Culture Collection (ATCC). Bradford protein assay kit was from Pierce Chemical Co. (Rockford, Ill.). Binding buffer used in the ligand binding assay contained 25 mM HEPES, 11.5 mM KCl, 11.5 mM NaCl, 6 mM $MgSO_4$, 1.8 mM $CaCl_2$ and 0.25% BSA.

Methods

Receptor cDNAs and Cell Lines

Cells expressing IL-8RA (CXC R1) and IL-8RB (CXC R2) receptor (IL-8A/CHO and IL-8B/CHO) were obtained as follows:

CHO CXC R1 and CXC R2 cell lines were prepared by cationic lipopolyamine (lipofectamine, GIBCO BRL) mediated transfection of CHO-K1 cells (ATCC) with pCDNAIII plasmids encoding the sequences of human CXC R1 or CXC R2. Cells were cultured under G418 selection (1 mg/ml) in DMEM, 10% fetal bovine serum, 2 mM L-glutamine, and 2% non-essential amino acids and clonal lines expressing the highest receptor levels were maintained for use in these experiments. The human CXC R1 receptor CDNA was cloned from HL-60 cell (ATCC) mRNA. (Clones encoding CXC R1 are described in Ahuja et al., (1992) *Nature Genetics* 2:31). First-strand cDNA was synthesized using M-MLV reverse transcriptase (Promega Riboclone™ cDNA synthesis system) and CXC RA cDNA was amplified by polymerase chain reaction using primers, 5' CCGAATTC-GACATGTCAAATATTACAGATCC3' SEQ ID NO.:1 and 5' GCTCTAGATCAGAGGTTGGAAGAGAC3' SEQ ID NO.:2. The PCR product was digested with EcoRI+XbaI and ligated into EcoRI/XbaI/calf intestinal phosphatase-digested pcDNA3 vector (Invitrogen Corp. (San Diego, Calif.)). The DNA sequence of one candidate was confirmed using the Promega Silver Sequence™ method. To generate the human CXC R2 expression clone, an approximately 1.8 kb cDNA fragment was recloned from pBluescript clone BS-p3 (Murphy, P. M. and Tiffany, H. L. (1991) *Science* 253, 1280–1283) into the pcDNA3 vector, using EcoRI and XhoI.

Construction of an Expression Plasmid for humanIL-8 and Ser72Cys humanIL-8

The cDNA for the coding sequence of humanIL-8 (amino acids 1–72 of the mature IL-8) was isolated by PCR from human thymus cDNA (Clontech Laboratories, Inc., Palo Alto, Calif.). PCR primers were designed to generate the N-terminus of the monocytic form of IL-8 (i.e., using primers corresponding to the sequence Ser1-Ala2-Lys3 . . . ) (Hébert, C. A., et al. (1990) *J. Immunol.* 145, 3033–3040) and either wild-type (i.e., primers corresponding to the sequence . . . Ala69-Glu70-Asn71-Ser72) or cysteine-substituted variant C-terminus (i.e., primers corresponding to the sequence . . . Ala69-Glu70-Asn71-Cys72). Both coding sequences were introduced into the pET30b expression plasmid (Novagen). The constructs were introduced in the *E. coli* strain BL21(DE3) (Novagen).

Expression of Recombinant humanIL-8 and humanIL-8 ser72cys

The pET30b-humanIL-8 and pET30b-humanIL-8 Cys72 plasmids were used to transform competent *E. coli* strain BL21 (DE3) employing standard protocols (Novagen). Wild type and mutant IL-8 were produced in *E. coli* as inclusion bodies. The following purification methods were used for both proteins. Cells pelleted from a 1 L culture induced with 0.5 mM IPTG for 4 hrs. were resuspended in lysis buffer A (Tris-HCl, 5 mM pH 8.0; EDTA, 2 mM; Tween-20, 0.5%) to a concentration of approximately 5–10 ml per gram of cells and subjected to 3–4 freeze/thaw cycles and chromosomal DNA sheared by repeated passage through syringe needles of increasing gauge. Insoluble material was collected by centrifugation and pellets were resuspended in urea wash buffer (Tris-HCl, 20 mM, pH 8.0; urea, 0.75 M; Tween-20, 0.5%) and centrifuged (85,000×g for 20 min.). Resuspension in urea and centrifugation was repeated twice or until the clarified supernatant was colorless. The urea-washed pellet was taken up in 40 ml of 6 M guanidine-HCl, 20 mM PBS, pH 6.0 and resuspended until no further solubilization occurred, and centrifuged at 85,000×g for 1 hr at 4° C. The supernatant was dialyzed (Spectra/Por Membrane MWCO 2,000) against 20 mM sodium phosphate buffer pH 6.5 at 4° C. with buffer changes every 4 hours until guanidine was calculated to be below 1 uM. The resultant flocculate solution was centrifuged (23,000×g for 20 min. at 4° C.). The supernatant was carefully removed and stored at 4° C. until further purified by cation exchange chromatography.

Perfusion Cation-Exchange Chromatography

Perfusion chromatography was performed at room temperature using a BioCAD Perfusion Chromatography Workstation (PerSeptive Diagnostics Inc., Cambridge, Ma.) connected to an SF-2120 Super Fraction Collector (Advantec). Clarified dialysate (total protein ~45 mg) was loaded onto a POROS 20CM column (4.6 mmD/100 mmL). The sample was eluted with a NaCl gradient (0–800 mM NaCl over 20 column volumes) buffered with 20 mM sodium phosphate, pH 6.5. The IL-8 was eluted at ~400 mM NaCl. The column flow rate was 10 ml/min (3600 cm/hr) and the UV monitor set a 280 nm. The fraction sizes were 1 ml of which 2 µl samples were analyzed on a 16% Tris-Gly SDS-PAGE gel (Novex) to ascertain purity. Protein concentration was determined for each fraction using the Bradford method. (Bradford, M. (1976) *Anal. Biochem.* 72, 248–254) BSA was used for the standard curve.

HPLC Conditions

Purification of IL-8 and IL-8ser72cys and analysis of the labeling reaction by reverse phase HPLC were carried out using a Dynamax HPLC System (Ranin). The column was a Phenomenex C5 Jupiter 300 (particle size: 5 um; stationary phase: C5; pore size: 300 Å; 250×4.6 mm). The mobile phase was water, 0.1% TFA (A)/acetonitrile, 0.1% TFA (B) The gradient was linear from 20–60% B at 1%/min. For analysis of labeling reactions 200–500 pmol of sample was injected. For purification of IL-8 or IL8cys72 samples ranging from 1–30 nmol (8–240 ug) were injected. Separations were monitored at both 215 and 280 nm. For purification of proteins, peaks were collected by hand, flash frozen and dried on a Speed Vac™ (Savant instruments).

Preparation of IL-8-Cys72-DTTA-E$^{+3}$

To 300 nmol (227 ug) Eu-N1-iodoacetamide (Wallac; 756.3 g/mol; $C_{21}H_{25}N_4O_9EuI$) was added 160 µg (19 nmol in 40 µl of PBS) of huIL-8ser72cys. The reaction was studied at two pHs, 7.5 and 8.5. The tube was vortexed and placed at ambient temperature. Aliquots (1 µl, ~0.5 nmol) were removed at indicated times to monitor labeling progress by HPLC. When the reaction was judged complete the sample was diluted 10-fold into Tris-buffered saline (TBS), pH 7.5 and dialyzed (Spectra/Por MWCO 2000) against TBS (4×4 L) at 4° C. to remove excess DTTA-Eu$^{3+}$ label. The protein concentration was determined using (BSA standard) and the specific activity was determined using a Europium standard solution supplied by Wallac.

Ligand Binding Assay

CHO cells expressing either CXC R1 or CXC R2 were seeded in a 96-well tissue culture plate (Costar) for Europium-based assays or in a 96-well opaque-wall/black mask tissue culture plate (EG & G Wallac) for $^{125}$I-based assays. Confluent cells (~40,000 cells/well) were washed with binding buffer and incubated with ligands in a 50 ml/well reaction volume for 1 h at room temperature. Depending on whether [$^{125}$I] IL-8 or IL-8-Cys72-DTTA-Eu$^{+3}$ was used, 80 µl/well of Optiphase scintillation fluid or 80 µl/well Enhancement solution was added to the microtiter plate and the plate put on a plate shaker for 5 min. For scintillation counting, the plate was counted in a Wallac Microbeta™ counter. For time-resolved fluorescence counting, the plate was counted in a DELFIA™ Fluorometer (Model 1234, EG & G Wallac). The Europium counting protocol was used and employed a 320 nm excitation pulse at a frequency of 1000s$^{-1}$ and detection at 615 nm (emission wavelength). Specific fluorescence was measured after a 400 msec time delay (for decay of background fluorescence) for 400 msec between each excitation pulse.

Mass Spectrometry

Mass spectra were obtained on a Finnigan MAT LCQ spectrophotometer.

Data Analysis

Ligand binding data were analyzed by non-linear least-square regression using the GraphPad Prizm computer program.

Protein Expression, Purification and Characterization

Figure 3:
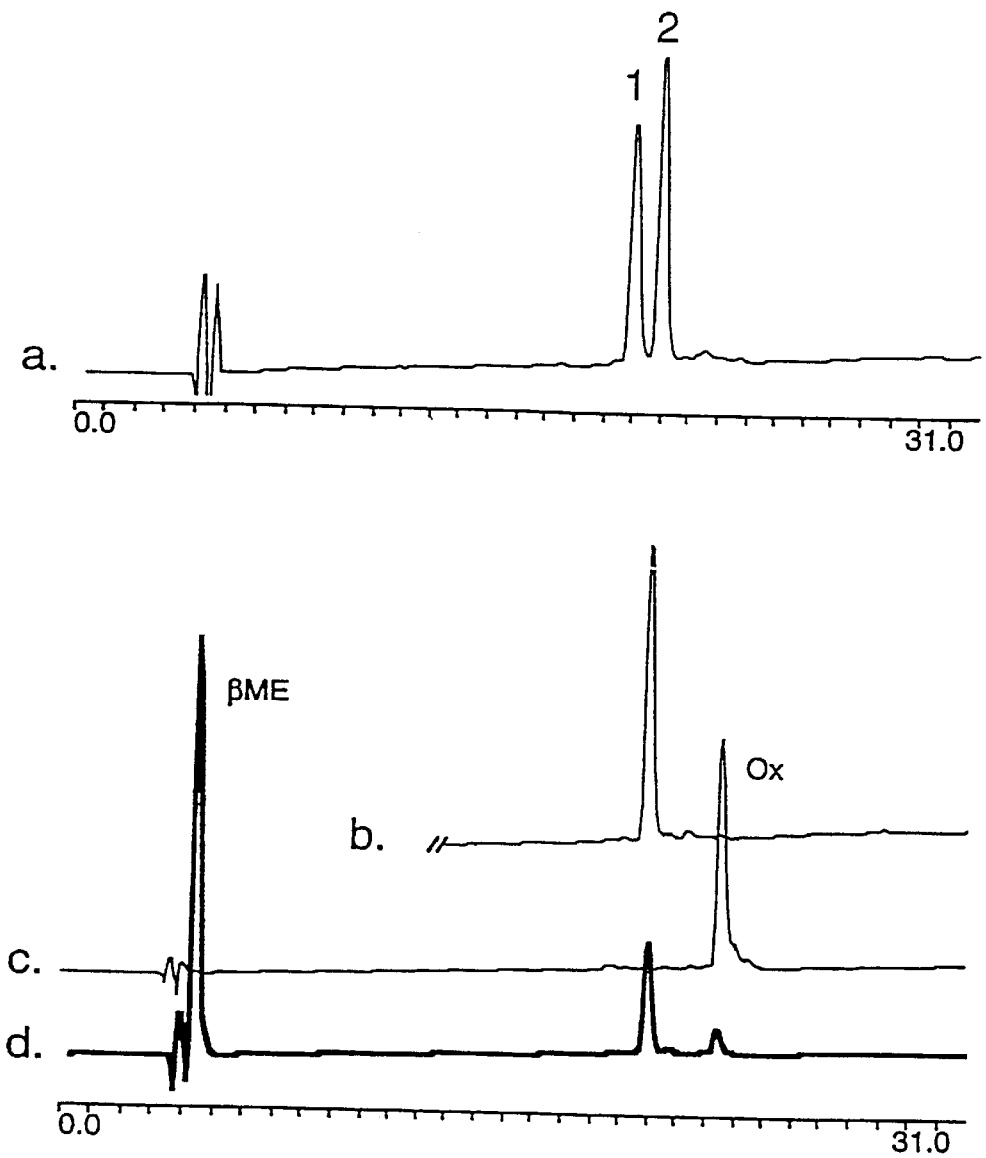

The bacterial expression and purification of IL-8 has been reported previously (Furuta, R., et al. (1989) *J. Biochem.* 106, 436–441). The preparation of IL8cys72 has been determined to result in a comparable yield to that obtained for wild type IL-8. For example, one liter of cells resulted in ~30 mg of >90% pure IL-8 or IL8cys72 as assessed by HPLC and SDS-PAGE analysis. Purification to homogeneity was accomplished on small amounts using HPLC. The single substitution of the carboxyl terminal serine72 by cysteine resulted in a shift in retention time (+0.9 min.) on reverse phase HPLC (FIG. 3a). Intermolecular disulfide oxidation of cys72 in the mutant IL-8 (IL-8cys72$^{ox}$) has been observed to occur slowly over time at pH 6.5 or rapidly when the pH of the buffer is above 7.0. Formation of this species is easily detected by an increase in retention time of 2.8 minutes on HPLC (FIG. 3b&c). Storage of the ser72cys mutant at pH 6.5 in phosphate buffer ([NaCl]~200 mM) at a concentration of 1 mM for about 1 year at 4° C. resulted in 34% conversion to the oxidized form. Oxidation of cys72 can be converted to the reduced form (IL-8cys72) by incubation with 1 mM β-mercaptoethanol (βME). The βME can be removed by rechromatographing on HPLC (FIG. 3d). The dimeric nature of this species is confirmed by migration of IL-8cys72$^{ox}$ on a non-reducing SDS gel at a mass approximately twice that of IL-8 or IL-8cys72. Mass spectroscopy experiments confirmed that IL-8cys72$^{ox}$ formed a dimer.

The cys72 mutant was shown to have identical binding properties to wild type IL-8 that was prepared by the same expression and purification scheme when assayed for its ability to compete with [$^{125}$I]IL-8 on recombinantly expressed CXCR1 or CXCR2. Results are shown in FIG. 4.

Labeling with Eu-DTTA Iodoacetamide

IL-8cys72 was labelled with Eu-DTTA iodoacetamide under two pH conditions (pH 7.5 and 8.5) at a molar ratio of protein: iodoacetamide of 1:15. Analysis of the reaction products by HPLC indicated that the conjugate of IL-8cys72 with Eu-DTTA (IL-8-cys72-DTTA-Eu$^{+3}$) formed essentially quantitatively at both pHs, although a 2-fold increase in reaction rate occurred at the higher pH. The major product, IL-8cys72-DTTA-Eu$^{+3}$, eluted on HPLC 1.4 minutes earlier than the unmodified IL-8cys72. By-products included oxidized IL-8cys72 (i.e., IL-8cys72$^{ox}$; ~3% at pH 7.5 and ~5% at pH 8.5) and approximately 10–16% of a possibly more highly conjugated product appearing as a shoulder on the product peak. Increased reactivity of lysine and histidine can be expected in the pH range of 7 and higher but accompanying increases in thiolate concentration hasten cysteine reactivity as well, and may explain the similar product and by-product ratios seen at the two pHs studied.

Characterization of Eu-labelled IL-8

The specific activity of IL-8-cys72-DTTA-Eu$^{+3}$ was determined to be 4.5×10$^6$ cps/pmol. This value indicates that IL-8-cys72 is labelled with ~1 Eu$^{3+}$ ion per molecule (spec. act. of Eu$^{3+}$=3.6±0.8×10$^6$ cps/pmol, n=11). Absolute cps are dependent on instrument settings and enhancement buffer composition, both of which were optimized by the manufacturer. For comparison, [$^{125}$I]IL-8 has a specific activity of 4.5×10$^6$ cps/pmol.

Europium-labelled and radiolabelled IL-8 were compared in identical binding conditions, using CHO cell clones harboring CXCR1 or CXCR2. IL-8cys72-DTTA-Eu$^{3+}$ showed saturable binding to both receptors, and the dissociation constants of both ligands were in agreement (see FIG. 4). Likewise, the B$_{max}$ determined using both ligands were similar.

In addition to showing specific, saturable binding, IL-8cys72-DTTA-Eu$^{3+}$ can be displaced by unlabelled chemokines with the expected potencies. Groα is a CC chemokine that has greater affinity for CXC R2 than for CXC R1. In displacement experiments, IL-8 and GROα were equipotent at displacing IL-8cys72-DTTA-Eu$^{3+}$ from CXC R2, while GROα was ~70-fold less potent than IL-8 at displacing Eu-IL-8 from CXC R2. Thus, IL-8cys72-DTTA-Eu$^{3+}$ and [$^{125}$I]IL-8 identify the same binding sites and exhibit the same pharmacological properties.

Modification of IL-8cys72 by another iodoacetamide reagent (biotin) resulted in a IL-8 bioconjugate with an affinity similar to that of wild type and Eu-labelled IL-8. FIG. 4 shows the value obtained for K$_i$(IL8cys72-biotin). Thus, modification of the carboxyl terminus of IL-8 according to the present invention can be performed using a wide range of moieties with little effect on receptor binding.

Thus, the site-specific labeling of IL-8 with Eu-DTTA according to the present invention resulted in a reagent exhibiting a detection sensitivity equivalent to [$^{125}$I]IL-8 in measuring CXCR1 and CXCR2 receptors on whole cells. The Eu labelled IL-8 retained binding properties despite the fact that IL-8 activity usually is sensitive to chemical modifications.

Replacing the carboxyl terminal serine of IL-8 with cysteine allowed generation of a ligand with a single free cysteine which reacted specifically with an iodoacetamide derivative of Eu-DTTA. Because IL-8 contains two intramolecular disulfide bonds there was substantial potential for disulfide bond scrambling with the additional engineered cysteine. Substitution of the cysteine, however, did not prevent formation of acceptable amounts of properly folded IL-8 product.

The carboxyl-terminal cysteine oxidizes over time. It has also been determined, however, that the resulting disulfide can be reduced with βME without reducing the structural intramolecular disulfide bonds of IL-8. The specific activity of the Europium-labelled ligand does not decay with time and has been stored for over one year with no loss in activity.

In sum, these results demonstrate successful site-specific labeling of IL-8 at its carboxy terminus. This bioconjugate retains the binding properties of the unmodified ligand and can be used in place of [$^{125}$I]-labelled IL-8 in high throughout screening. Furthermore, the labelled IL-8 does not display the limited shelf-life of radiolabelled IL-8.

EXAMPLE 2

Formation of Cy5 Labelled IL-8

Human interleukin-8, Ser72→Cys mutant (IL-8cys72) was cloned as described above. Monofunctional Cy5-iodoacetamide was obtained from Amersham Life Sciences, Inc. (Arlington Heights, Ill.). To 500 nM Cy5-iodoacetamide was added 200 nmol (200 μl of a 1 mM stock) of hIL-8 (S72C) in 20 mM sodium phosphate, pH 6.5, 400 mM NaCl. The tube was vortexed and placed in the dark at ambient temperature. HPLC analysis indicated that after 48 hours the reaction was complete. The product was purified (2×100 μl injections) from unreacted Cy5-iodoacetamide and oxidized IL-8cys72 by HPLC. Sample was reconstituted in 50 mM sodium phosphate, pH 7.2 at an estimated concentration of 400 μM. A more accurate concentration was then determined from a fluorescence spectrum of an aliquot of this sample. Further characterization indicated that IL-8cys-Cy5 had a mobility similar to wild type IL-8 on a 16% SDS-PAGE analysis and displayed a K$_i$ of 2 nM in a conventional [$^{125}$I]IL-8 ligand displacement assay employing CXC R2 receptor. This was similar to the value obtained using [$^{125}$I]IL-8 ligand. Thus, Cy5 labelled IL-8 according to the invention retained its affinity for receptor.

We claim:

1. A polypeptide comprising a chemokine receptor binding sequence, said polypeptide being detectably labelled with a label other than a radiolabel at a cysteine residue substituted for an amino acid contained in its C-terminal sequence, said C-terminal sequence forming an α-helix structure.

2. The polypeptide of claim 1 wherein said chemokine is a CXC chemokine.

3. The polypeptide of claim 2 wherein said CXC chemokine is selected from the group consisting of SDF-1, IL-8, GROα, GROβ, GROγ, NAP-2, ENA78, GCP2, PF4, IP10, Mig, CKα1, and CKα2.

4. The polypeptide of claim 1 wherein said chemokine is a CC chemokine.

5. The polypeptide of claim 4 wherein said CC chemokine is selected from the group consisting of MCP-1, MCP-3, Eotaxin, MCP-2, MCP-4, CFβ6, I-309, MIP-1α, MIP-1β, CKβ7, HCC-1, HCC-3, HCC-2, CDβ8, RANTES, CKβ12, TARC, CKβ13, CKβ4, CKβ11, and CKβ9.

6. A polypeptide comprising the receptor binding sequence of IL-8, said polypeptide being detectably labelled with a label other than a radiolabel at a cysteine residue substituted for an amino acid contained in its C-terminal sequence, said C-terminal sequence forming an α-helix structure.

7. The polypeptide of claim 6 comprising β-pleated sheet sequences from amino acids 10 to 51 of IL-8.

8. The polypeptide of claim 6 comprising the amino acid sequence of IL-8 having fewer than 10 conservative amino acid substitutions.

9. The polypeptide of claim 6 comprising the amino acid sequence of IL-8 having fewer than 3 conservative amino acid substitutions.

10. The polypeptide of claim 6 having the sequence of IL-8 wherein said C-terminal region comprises the six C-terminal amino acids of the amino acid sequence of IL-8 and said cysteine is substituted for one of said six amino acids.

11. The polypeptide of claim 6 wherein said polypeptide binds to an IL-8 receptor with substantially the same affinity as IL-8.

12. The polypeptide of claim 6 wherein said label is selected from the group consisting of a fluorescent label, an enzyme label, and a chemiluminescent label.

13. The polypeptide of claim 12 wherein said label is a fluorescent label.

14. The polypeptide of claim 13 wherein said label is a lanthanide chelate.

15. A polypeptide having the amino acid sequence of IL-8 with a cysteine residue substituted for an amino acid contained in its carboxy terminal amino acids nos. 54–72, wherein said cysteine residue is detectably labelled with a label other than a radiolabel.

16. The polypeptide of claim 15 wherein said detectably labelled cysteine is substituted for a serine at amino acid 72 of said IL-8.

17. The polypeptide of claim 16 wherein said label is a lanthanide chelate.

18. A method of determining the affinity of a compound for a receptor for a CC or CXC chemokine, said method comprising the steps of:

(a) contacting said compound with said receptor in the presence of the labelled polypeptide of claim 1; and (b) determining binding of said polypeptide to said receptor by determining the presence of said label.

19. The method of claim 18 wherein said assay comprises a homogeneous assay.

20. The method of claim 18 wherein said assay comprises a heterogeneous assay.

21. In a competitive assay for determining binding of a compound to a receptor for which interleukin-8 (IL-8) is a ligand, wherein said compound and a polypeptide having the binding affinity of IL-8 for said receptor compete for said binding, further wherein said polypeptide is labelled and binding of said compound is determined by measuring the amount of label bound to said receptor, the improvement wherein said polypeptide comprises the receptor binding sequences of interleukin-8 (IL-8) and is detectably labelled with a label other than a radiolabel at a cysteine contained in its C-terminal 19 amino acids.

* * * * *

UNITED STATES PATENT AND TRADEMARK OFFICE
CERTIFICATE OF CORRECTION

PATENT NO. : 6,156,520
DATED : December 5, 2000
INVENTOR(S) : Inglese et al.

It is certified that error appears in the above-identified patent and that said Letters Patent are hereby corrected as shown below:

Item [73] Assignee: Delete "Cranbury" and replace with - -Princeton- -

Signed and Sealed this

First Day of May, 2001

Attest:

NICHOLAS P. GODICI

Attesting Officer      Acting Director of the United States Patent and Trademark Office

SEQUENCE LISTING

```
<160> NUMBER OF SEQ ID NOS: 2

<210> SEQ ID NO 1
<211> LENGTH: 31
<212> TYPE: DNA
<213> ORGANISM: HL60 Cells

<400> SEQUENCE: 1
ccgaattcga catgtcaaat attacagatc c                              31

<210> SEQ ID NO 2
<211> LENGTH: 26
<212> TYPE: DNA
<213> ORGANISM: HL60 Cells

<400> SEQUENCE: 2
gctctagatc agaggttgga agagac                                    26
```